United States Patent
Jahn

(10) Patent No.: US 8,801,435 B2
(45) Date of Patent: Aug. 12, 2014

(54) SCANBODY FOR DETECTING THE POSITION AND ORIENTATION OF A DENTAL IMPLANT

(75) Inventor: Dirk Jahn, Weyher (DE)

(73) Assignee: NT-Trading GmbH & Co. KG, Karlsruhe (DE)

( * ) Notice: Subject to any disclaimer, the term of this patent is extended or adjusted under 35 U.S.C. 154(b) by 59 days.

(21) Appl. No.: 13/306,092

(22) Filed: Nov. 29, 2011

(65) Prior Publication Data
US 2012/0135371 A1    May 31, 2012

(30) Foreign Application Priority Data
Nov. 29, 2010  (DE) .......................... 10 2010 062 105

(51) Int. Cl.
*A61C 8/00*    (2006.01)

(52) U.S. Cl.
USPC ......................................................... 433/173

(58) Field of Classification Search
USPC ............................... 433/172–176, 72, 215, 75
See application file for complete search history.

(56) References Cited

U.S. PATENT DOCUMENTS

| | | | |
|---|---|---|---|
| 5,782,918 A * | 7/1998 | Klardie et al. | 606/60 |
| 5,857,853 A | 1/1999 | van Nifterick et al. | |
| 6,287,119 B1 | 9/2001 | van Nifterick et al. | |
| 6,524,106 B1 | 2/2003 | Ziegler | |
| 2002/0018980 A1 * | 2/2002 | Yeung | 433/173 |
| 2008/0176188 A1 | 7/2008 | Holzner et al. | |
| 2011/0014585 A1 * | 1/2011 | Seo | 433/173 |

FOREIGN PATENT DOCUMENTS

| | | |
|---|---|---|
| EP | 0 776 183 | 6/1997 |
| EP | 1 920 730 A2 | 5/2008 |
| EP | 2 218 423 A1 | 8/2010 |
| WO | WO 2010/108919 A2 | 9/2010 |

OTHER PUBLICATIONS

Search Report of European Patent Office issued in European Application No. 11186800.6 with English translation of category of cited documents dated Mar. 7, 2013 (8 pages).
Examination Report issued by the German Patent Office in German Application No. 10 2010 062 105.6-43 dated Mar. 3, 2011 (5 pages).

* cited by examiner

*Primary Examiner* — Sunil K Singh
(74) *Attorney, Agent, or Firm* — Flynn, Thiel, Boutell & Tanis, P.C.

(57) ABSTRACT

Scanbody for detecting the position and orientation of a dental implant. A scanbody including a bottom section capable of being connected to an implant, and also a three-dimensional scannable region having an asymmetrical geometry permitting unequivocal detection of its surface from different scanning directions in relation to a longitudinal center axis of the scanbody. The scannable region is provided, on its peripheral cylindrical surface, with scannable sections that are radially offset outwardly and/or inwardly in relation to the peripheral cylindrical surface, each of which scannable sections is differently shaped from the other scannable sections.

14 Claims, 3 Drawing Sheets

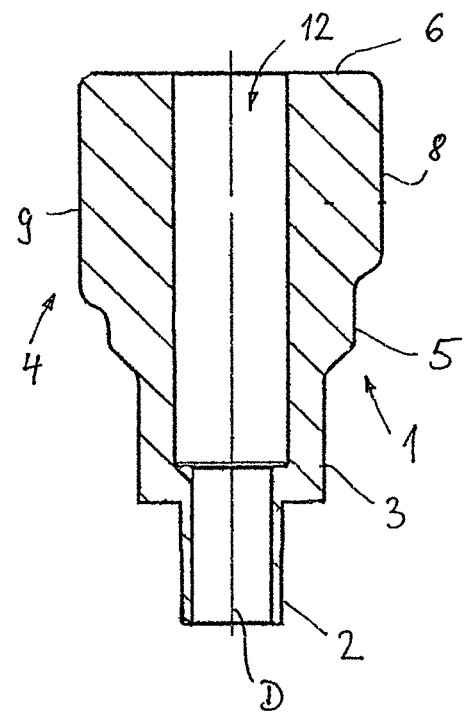
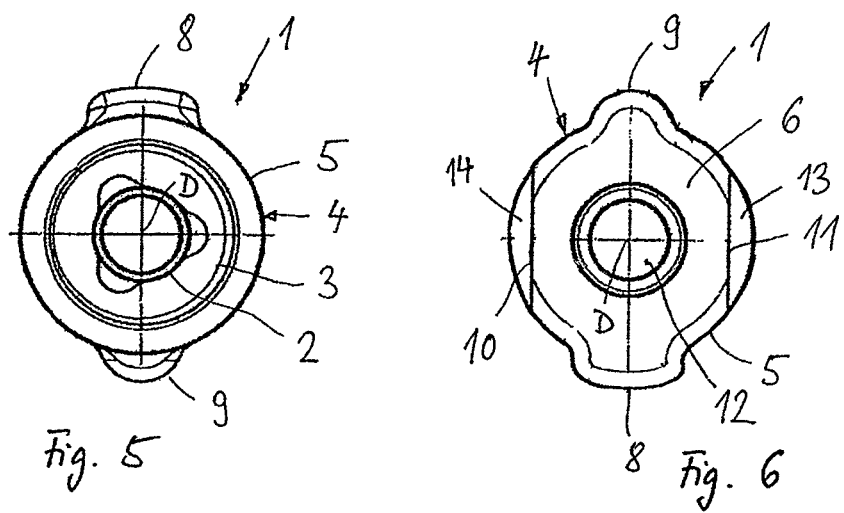

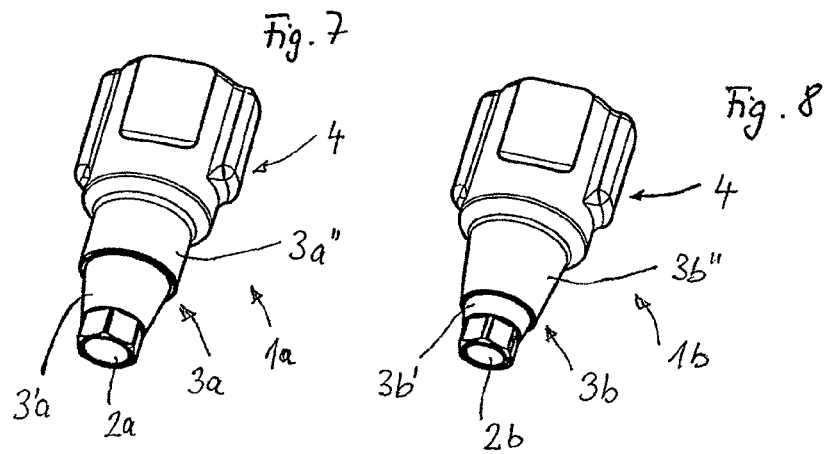
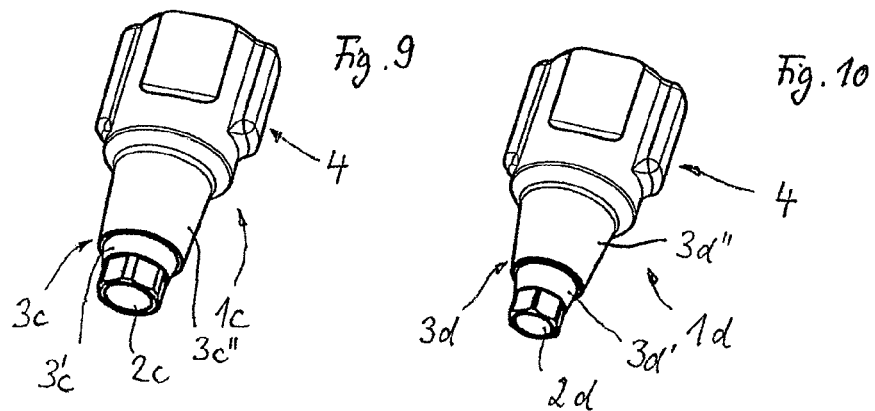
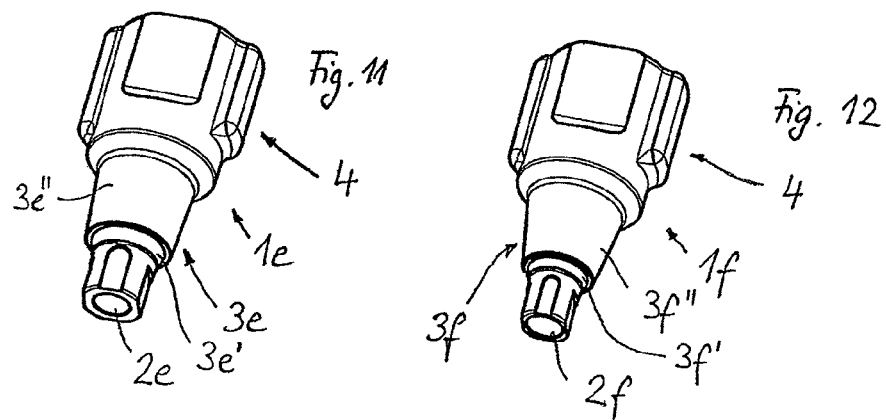

SCANBODY FOR DETECTING THE POSITION AND ORIENTATION OF A DENTAL IMPLANT

CROSS REFERENCE TO RELATED APPLICATION

This application claims the priority of the German patent application No. 10 2010 062 105.6. The whole disclosure of this prior application is herewith incorporated by reference into this application.

FIELD OF THE INVENTION

The present invention relates to a scanbody for detecting the position and orientation of a dental implant, which scanbody comprises a bottom section capable of being connected to the implant, and a three-dimensional scannable region that has an asymmetrical geometry permitting unequivocal detection of its surface from different scanning directions in relation to the longitudinal center axis of the scanbody.

BACKGROUND OF THE INVENTION

A scanbody of such type is disclosed in EP 2 218 423 A1. The scanbody disclosed is in the form of a single-part component and comprises a bottom section capable of being connected directly, or indirectly via an adaptor, to a dental implant. The scanbody comprises on its surface a three-dimensional scannable region provided with a number of flat surfaces that are oriented at angles to each other and that are triangular or pentagonal in shape.

SUMMARY OF THE INVENTION

It is an object of the present invention to provide a scanbody of the above type that makes it possible to carry out scanning from all scanning directions with a high degree of accuracy.

This object is achieved in that there is provided a transition region between the bottom section and the scannable region, which transition region is separate from the bottom section and from the scannable region, and the scannable region comprises a plurality of scannable contoured sections that are distributed around the periphery of the scannable region and that protrude outwardly in the radial direction beyond the external surface of the transition region and that are each shaped differently from each other. Due to the solution proposed by the invention, the interposition of a transition region between the bottom section and the scannable region results in the scannable region being located at a distance from the bottom section and thus from an implant such that it is possible to carry out scanning from any scanning direction. Moreover, the scannable contoured sections that protrude in the radial direction beyond the external surface of the transition region and that are shaped differently from each other also ensure that the scanbody is accurately detected from all scanning directions. The fact that the scannable contoured sections are radially broader than the transition region means that the scannable region has a large volume and thus a large surface area such as is conducive to very accurate measurement. As a result, it is very easy to precisely ascertain the orientation of the longitudinal center axis of the dental implant in all three directions in space. The precisely ascertained, three-dimensional scan findings are compared with original data pertaining to the scanbody as obtained from an electronic image library. By means of this comparison, it is possible to very precisely ascertain the orientation of the implant, particularly in relation to the gingiva, the adjacent teeth, the jaw area, or adjacent dental prosthetic items or implants. As a result, the designs of abutments and dental prosthetic items that are dependent on the results of the scanning procedure can be adjusted and customized very precisely. The high precision of the scanning procedure will necessarily ensure a high degree of precision in the subsequent processes involved in customizing abutments and dental prosthetic items, since such processes are dependent on the scan results. As a result of the solution proposed by the invention, scanning the scanbody can be carried out not only from above or from the side but also obliquely from below. This is particularly advantageous, since a scanbody is frequently poorly accessible when it is scanned directly in a patient's mouth. By virtue of the fact that the scanbody can be scanned from below, it is in all cases possible to carry out unequivocal and three-dimensional detection of the scanbody and its environment in a patient's mouth. Of course, the scanbody also offers advantages when a model of a dental arch comprising an appropriately prepared dental implant is scanned. According to the invention, there is provided a transition region which adjoins the bottom section in the axial direction and which is in turn adjoined by the scannable region located opposite the bottom section in the axial direction, and the periphery of the scannable region is expanded in the radial direction so as to be broader than the transition region. Preferably, the scanbody is made of a scannable plastics material, more particularly a thermoplastics material. Very advantageously, the scanbody is made of polyether ether ketone (PEEK).

In one embodiment of the invention, the scannable region is provided on its peripheral cylindrical surface with scannable contoured sections that are, relatively to the longitudinal center axis, radially offset outwardly and inwardly in relation to the peripheral cylindrical surface.

In a further embodiment of the invention, the scannable region is provided on its peripheral cylindrical surface with scannable contoured sections in the form of scannable profiles that protrude outwardly in the radial direction and scannable surfaces that are offset inwardly in the radial direction. Preferably, the scannable surfaces are flat. The scannable profiles protrude outwardly in the radial direction.

In a further embodiment of the invention, the scannable profiles and the scannable surfaces have longitudinal orientations that are parallel to the longitudinal center axis of the scanbody. Since the longitudinal center axis of the scanbody necessarily also defines the longitudinal center axis of the dental implant, the position of the longitudinal center axis of the dental implant can be inferred from the ascertained location of the scannable profiles and scannable surfaces.

In a further embodiment of the invention, the peripheral cylindrical surface of the scannable region is axially symmetric to, and more particularly cylindrically coaxial with, the longitudinal center axis, and the cylinder diameter is greater than the diameter of the transition region. This embodiment also contributes towards simplifying the process of detecting the position and orientation of the dental implant.

In a further embodiment of the invention, the scannable profiles have a cam shape that protrudes outwardly in the radial direction. Preferably, corresponding cams have different axial lengths and widths. It is also possible for the cams to have either different axial lengths or different axial widths. The cams have the same cross-section over the entire length thereof. Preferably, the cams have a convexly curved cross-section.

In a further embodiment of the invention, an end face of the scannable region opposing the bottom section is flat and is oriented in a radial plane in relation to said longitudinal center axis of the scannable region. Preferably, the scannable region has the basic shape of a cylinder, while its end face is shaped so as to correspond to the end face of a cylinder.

In a further embodiment of the invention, the cam-like scannable profiles have different axial lengths and/or widths and/or radial distances. This provides unequivocal allocation of the scannable region in three-dimensional space.

In a further embodiment of the invention, the scannable surfaces are flat. The flat shape applies to the large-area regions of the scannable surfaces. Preferably, the marginal areas of the scannable surfaces are concavely curved or form definite edges on the peripheral cylindrical surface.

In a further embodiment of the invention, there are provided two scannable surfaces that are diametrically opposed to each other and have different axial lengths and/or widths. In this way, the orientation of the scanbody can be unequivocally ascertained.

In a further embodiment of the invention, the end face of the scannable region located in the radial plane is provided with a screw bore for attachment of the scanbody to the implant or to an adaptor connected to the implant. This makes it possible to releasably fix the scanbody to the dental implant, or to an adaptor connected to the implant, in a simple manner.

In a further embodiment of the invention, the transition region is cylindrical in shape. Preferably, the cylindrical shape is coaxial with the longitudinal center axis of the scanbody so that the position of the longitudinal center axis of the dental implant can be inferred from the position of the transition region itself. By virtue of the fact that the transition region has a smaller diameter than the scannable region, the transition region cannot conceal the scannable region when the viewing direction is from below, that is, when scanning is carried out from below. Rather, the scannable region can also be viewed and detected unequivocally when scanned from below.

In a further embodiment of the invention, the transition region expands, starting from the bottom section, toward the scannable region. Preferably, the transition region is configured to expand continuously and is very preferably conical.

BRIEF DESCRIPTION OF DRAWINGS

Additional advantages and features of the invention are revealed in the claims and the following description of a preferred exemplary embodiment of the invention that is explained with reference to the drawings, in which:

FIG. 1 is a perspective view of an embodiment of a scanbody of the invention in, FIG. 4 is a longitudinal cross-section of the scanbody shown in FIGS. 1 to 3, FIG. 5 is a bottom view of the scanbody shown in FIGS. 1 to 4, FIG. 6 is a top view of the scanbody shown in FIGS. 1 to 5, and FIGS. 7 to 12 show various embodiments of the scanbody of the invention that are similar to that shown in FIG. 1.

DETAILED DESCRIPTION

Figure 1:
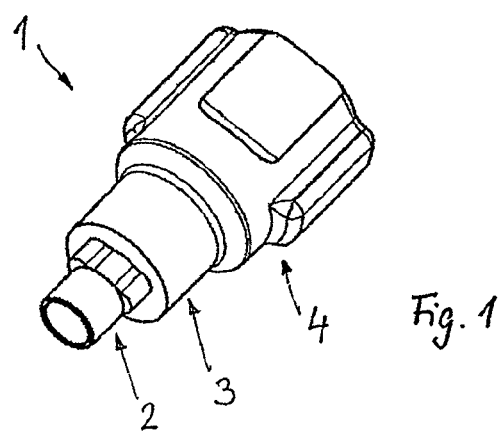
Figure 2:
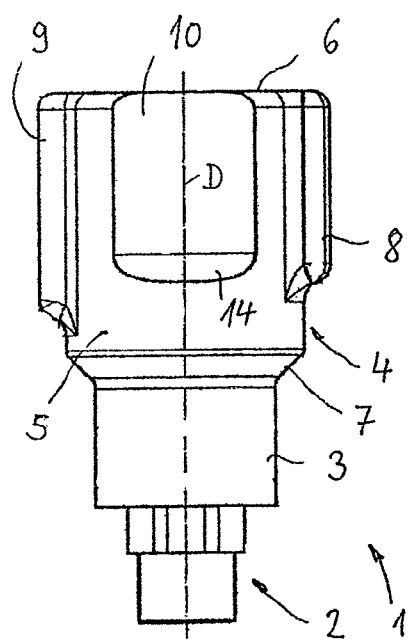
FIG. 2 is an enlarged side view of the scanbody shown in FIG. 1.
Figure 3:
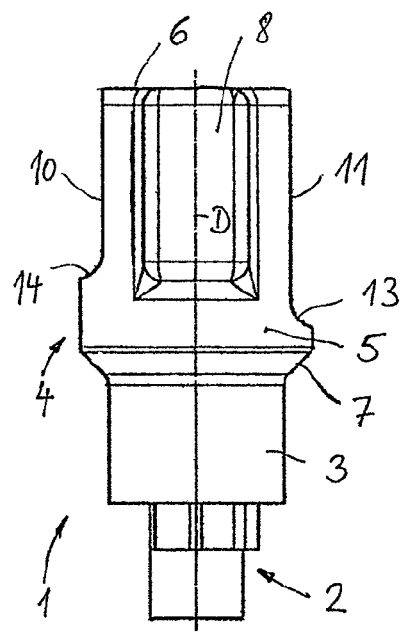
FIG. 3 shows the scanbody shown in FIG. 2 in a side view rotated through 90°.

A scanbody 1 as shown in FIGS. 1 to 6 is in the form of a single-part plastics component made of a thermoplastics material PEEK (polyether ether ketone). The scanbody 1 is used for detecting the position and orientation of a dental implant in the jaw area of a patient. The process of detecting the position and orientation of the dental implant serves to assist the planning of customized abutments and the fabrication of customized dental prosthetic items. The scanbody can be detected precisely in three dimensions by means of appropriate intraoral scanning procedures capable of being carried out in a patient's mouth. Alternatively, the scanning procedures can be carried out extraorally on a planning model or a working model for a patient. In both cases, it is also possible to precisely associate the scanbody with the dental environment in the jaw area (mouth or model) such as the adjacent teeth, jaw subregions, dental implants, gingiva, and the like, in three dimensions. The scanbody 1 of the invention can be detected from all directions for complete association with the environment, in three dimensions. The scanbody 1 is connected either directly to the dental implant or to an adaptor on the dental implant. The scanbody 1 is removed on completion of the scanning procedure. The electronic data ascertained in the scanning procedure are evaluated and used for the planning and customization of an abutment or a dental prosthetic item.

The scanbody 1 comprises a bottom section 2 capable of being inserted into the top surface of the dental implant or into an adaptor on the dental implant and capable of being fixed thereon by means of a screw connection. The bottom section 2 comprises anti-rotation means (not shown in detail) that make it possible for the scanbody 1 to be positioned so as to be rotationally immovable in relation to the dental implant. The bottom section 2 forming the lowermost region of the scanbody 1 is adjoined by a cylindrical transition region 3 that is coaxial with the longitudinal center axis D of the scanbody 1. The diameter of the cylindrical transition region 3 increases in steps in relation to the substantially cylindrical bottom section 2. The bottom section 2, which is substantially in the form of a plug-in part, is provided with cam-like anti-rotation elements that protrude outwardly from the cylindrical bottom section 2 in the radial direction. Also in the region of the anti-rotation means is the diameter of the bottom section 2 smaller than that of the transition region 3. The transition region 3 is adjoined by a large-volume scannable region 4 at the end face 6 located opposite the bottom section 2, which scannable region 4 extends approximately over half the length of the scanbody 2 as measured along the longitudinal center axis D. The scannable region 4 comprises a cylindrical skirt 5 that is coaxial with the longitudinal center axis D and that has a larger diameter than the transition region 3. For the purposes of the present invention, the cylindrical skirt 5 is to be regarded as being tantamount to the peripheral cylindrical surface of the scanbody 1. The peripheral cylindrical surface 5 is delimited upwardly in its axial length, that is, away from the transition region 3, by an end face 6, which is in the form of a flat surface that is oriented in a radial plane relatively to the longitudinal center axis D. The cylindrical skirt 5 comprises, all in all, four scannable contoured sections 8 to 11 which are distributed uniformly around the periphery thereof and of which two are in the form of cam-like scannable profiles 8, 9 and the other two are in the form of substantially flat scannable surfaces 10, 11 that are offset inwardly in the radial direction. The cam-like scannable profiles 8, 9 extend in the longitudinal direction of the scanbody 1 and are thus parallel to the longitudinal center axis D. The top ends of the two scannable profiles 8, 9 are flush with the end face 6, and these scannable profiles 8, 9 extend downwardly over more than half the length of the scannable region 5. The scannable profile 9 is longer than the scannable profile 8 by approximately 10 to 20%. Both of the scannable profiles 8, 9 protrude outwardly from the cylindrical skirt 5 when viewed in the radial direction. When viewed in the peripheral direction of the scannable region 5, the width of the scannable profile 8 is substantially greater than that of the scannable profile 9. The two scannable profiles 8, 9 are located diametrically opposed to each other. The two scannable surfaces 10, 11 that are offset inwardly in the radial direction are located at right angles to the scannable profiles 8, 9 and are also diametrically opposed to each other in such a way that the flat areas of the scannable surfaces 10, 11 are parallel to each other and parallel to the longitudinal center axis D. The scannable contoured sections 8 to 11 are distributed uniformly around the periphery of the cylindrical skirt 5 such that adjacent scannable sections 8 to 11 are oriented at an angle of 90° to each other, when viewed in the peripheral direction.

The scanbody 1 is a solid plastics component that is provided at its center with a single stepped through bore 12 (FIG. 4), also referred to as a screw bore. This through bore serves to accommodate a screw that releasably fixes the scanbody 1 to the dental implant or to an assigned adaptor.

The two cam-like scannable profiles 8, 9 are provided at their corner regions with large radii so that they are convexly rounded. The broad scannable profile 8 has an approximately rectangular cross-section. The narrow scannable profile 9 has an approximately semicircular cross-section.

The mutually opposing flat scannable surfaces 10, 11 are offset inwardly in the radial direction in relation to the cylindrical skirt 5, and they are adjoined by the external cylindrical surface of the skirt 5 via the radii 13, 14 disposed in the region of each scannable surface 10, 11 and in the region of an underside of each scannable surface 10, 11 that is near to the transition region 3. The radii 13, 14 are in the form of concave regions. As can be seen from FIG. 6, the flat surface subregions extend toward mutually opposing longitudinal sides of each scannable surface 10, 11 to the external surface of the cylindrical skirt 5, where they merge into the corresponding external contoured surface via an edge. As can be seen from FIGS. 1 to 6, the scanbody 1 appears differently when viewed from different directions, and each appearance is unique and precisely defined in three dimensions and differs from any other appearance observed from any other direction. It is thus possible to detect the scanbody 1 precisely in three-dimensional space and thus also in a patient's mouth or in the region of a jaw model, and also to precisely ascertain the dental environment by way of distances, orientations, and alignments.

The scanbodies 1$a$ to 1$f$ shown in FIGS. 7 to 12 comprise scannable regions 4 that are identical to the scannable region 4 of the scanbody 1 shown in FIGS. 1 to 6. Therefore, reference is made to the description of the embodiment shown in FIGS. 1 to 6, to avoid repetition. The essential differences in the scanbodies 1$a$ to 1$f$ are, firstly, that the bottom sections 2$a$ to 2$f$ are adapted to match differently shaped insertion regions of different designs of dental implants. Thus the bottom sections 2$a$ to 2$d$ have a hexagonal profile, while on the other hand the bottom sections 2$e$ and 2$f$ are provided with groove and tongue profiles.

In all scanbodies 1$a$ to 1$f$, the transition regions 3$a$ to 3$f$ are stepped in the axial direction. At least one subregion of each transition region 3$a$ to 3$f$ expands conically in such a way that this subregion flares out from its end edge adjacent to the respective bottom section 2$a$ to 2$f$ toward the scannable region 4 continuously, namely conically. The second subregion can either likewise expand conically or it can be of a cylindrical shape. In the embodiment shown in FIG. 7, the lower subregion 3'$a$ near to the bottom section 2$a$ flares out conically. However, the adjoining subregion 3$a$" of the transition region 3$a$ extending upwardly in the axial direction toward the scannable region 4 is cylindrical in shape and has a diameter that increases in a step-like manner in relation to the conical subregion 3"$a$. In the embodiment shown in FIG. 8, the scanbody 1$b$ comprises two conical subregions 3$b'$, 3$b''$ that are separated from each other by means of a step. The lower conical subregion 3$b'$ starts at the bottom section 2$b$. The second conical subregion 3$b''$ adjoining the lower conical subregion upwardly in the axial direction flares out toward the scannable region 4. As in the case of the embodiment shown in FIG. 8, the scanbody 1$c$ shown in FIG. 9 likewise comprises two conical subregions 3'$c$, 3$c''$ in the transition region 3$c$, which two conical subregions 3'$c$, 3$c''$ are separated from each other by a step. The same applies to the scanbody 1$d$ shown in FIG. 10, the difference being that the lower, conically expanding subregion 3$d'$ has a slightly larger axial length than the lower subregions 3$b'$ and 3'$c$ shown in FIGS. 8 and 9 respectively.

In the embodiments shown in FIGS. 11 and 12, the lower, conically expanding subregions 3$e'$ and 3$f'$ have a relatively small axial length. The cone angle of each lower subregion 3$e'$, 3$f'$ is significantly larger than that of the adjoining conically expanding subregion 3$e''$, 3$f''$.

The scanbodies 1$a$ to 1$f$ shown in FIGS. 7 to 12 are perspective views drawn on a greatly enlarged scale.

The invention claimed is:

1. A scanbody for detecting the position and orientation of a dental implant comprising a bottom section capable of being connected to the implant, a three-dimensional scannable region having an asymmetrical geometry permitting unequivocal detection of a surface thereof from different scanning directions in relation to a longitudinal center axis of said scanbody, and a transition region between said bottom section and said scannable region, the transition region being separate from said bottom section and separate from said scannable region, and said scannable region having a plurality of scannable contoured sections which are distributed around a periphery of said scannable region and which protrude outwardly radially beyond an external contour of said transition region, each of said scannable contoured sections being differently shaped from the other scannable contoured sections, wherein the scannable contoured sections comprise four different scannable contoured sections, with each one of the four different scannable contoured sections being radially opposite another one of the four different scannable contoured sections.

2. The scanbody as defined in claim 1, wherein the surface of the scannable region comprises a peripheral cylindrical surface, the scannable contoured sections are on the peripheral cylindrical surface, and the scannable contoured sections are radially offset from the peripheral cylindrical surface outwardly and inwardly in relation to said longitudinal center axis.

3. The scanbody as defined in claim 1, wherein the surface of the scannable region comprises a peripheral cylindrical surface and the scannable contoured sections comprise scannable profiles protruding radially outwardly and scannable surfaces offset radially inwardly on the peripheral cylindrical surface of said scannable region.

4. The scanbody as defined in claim 3, wherein said scannable profiles and said scannable surfaces have longitudinal orientations that are parallel to said longitudinal center axis of said scanbody.

5. The scanbody as defined in claim 1, wherein the scannable contoured sections are on a peripheral cylindrical surface on said scannable region, said peripheral cylindrical surface of said scannable region is axially symmetrical to said longitudinal center axis, and a diameter of the surface of the scannable region is greater than a diameter of the transition region.

6. The scanbody as defined in claim 3, wherein said scannable profiles have a radially protruding cam shape.

7. The scanbody as defined in claim 1, wherein an end face of the scannable region opposing said bottom section is flat and is oriented in a radial plane relatively to said longitudinal center axis.

8. The scanbody as defined in claim 6, wherein said cam shape of said scannable profiles have different axial lengths and/or widths and/or radial distances in relation to said longitudinal center axis.

9. The scanbody as defined in claim 3, wherein said scannable contoured sections are flat.

10. The scanbody as defined in claim 9, wherein the scannable contoured sections have different axial lengths and/or widths.

11. The scanbody as defined in claim 7, wherein said end face of the scannable region situated in the radial plane is provided with a screw bore for attachment of said scanbody to the implant or to an adapter connected to the implant.

12. The scanbody as defined in claim 1, wherein said transition region is of a cylindrical shape.

13. The scanbody as defined in claim 1, wherein said transition region expands from said bottom section toward said scannable region.

14. The scanbody as defined in claim 1, wherein the four different scannable contoured sections comprise a first pair of oppositely facing contoured sections and a second pair of oppositely facing contoured sections, the first pair of oppositely facing contoured sections have flat faces of different lengths and the second pair of oppositely facing contoured sections have radially protruding profiles of different dimensions.

* * * * *